US007262176B2

(12) United States Patent
Elzein et al.

(10) Patent No.: US 7,262,176 B2
(45) Date of Patent: Aug. 28, 2007

(54) ADENOSINE $A_3$ RECEPTOR AGONISTS

(75) Inventors: Elfatih Elzein, Fremont, CA (US); Venkata Palle, Gurgoan (IN); Vaibhav Varkhedkar, San Diego, CA (US); Jeff Zablocki, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 287 days.

(21) Appl. No.: 10/722,702

(22) Filed: Nov. 25, 2003

(65) Prior Publication Data

US 2004/0116376 A1    Jun. 17, 2004

Related U.S. Application Data

(63) Continuation-in-part of application No. 10/212,896, filed on Aug. 5, 2002, now abandoned.

(60) Provisional application No. 60/311,069, filed on Aug. 8, 2001.

(51) Int. Cl.
*A01N 43/04* (2006.01)
*A61K 31/70* (2006.01)

(52) U.S. Cl. ............................ 514/46; 514/45; 514/47; 514/263.2; 536/27.3; 536/27.6; 536/27.61; 544/277

(58) Field of Classification Search ................. 514/45, 514/46, 47, 263.2; 536/27.3, 27.6, 27.67, 536/27.7; 544/277
See application file for complete search history.

(56) References Cited

U.S. PATENT DOCUMENTS

| | | | |
|---|---|---|---|
| 6,214,807 B1 * | 4/2001 | Zablocki et al. | 514/46 |
| 6,770,634 B1 * | 8/2004 | Zablocki et al. | 514/46 |
| 6,855,818 B2 * | 2/2005 | Zablocki et al. | 536/27.3 |

FOREIGN PATENT DOCUMENTS

| | | |
|---|---|---|
| WO | WO 00/78777 | 12/2000 |
| WO | WO 00/78778 | 12/2000 |
| WO | WO 00/78779 | 12/2000 |

OTHER PUBLICATIONS

Klotz et al. Naunyn-Schmiedeberg's Arch Pharm (1999), 360, 103-108.*
Klotz et al: "2-Substituted N-Ethylcarboxamidoadenosine Derivatives as High-Affinity Agonists at Human A3 Adenosine Receptors", Nauny-Schmiedeberg's Archives of Pharmacology, Springer, Berlin, DE., vol. 360, No. 2, 1999, pp. 103-108 XP000984051, ISSN: 0028-1298, compound 8, tables 1,2.
Baraldi et al: "Novel N6-(Substituted-phenylcarbamoyl) Adenosine-5'-Uronamides as Potent Agonist for A2 Adenosine Receptors", Journal of Medicinal Chemistry, American Chemical Society, Washington, US, vol. 39, No. 3, Feb. 1996, pp. 802-806, XP002913657, ISSN: 0022-2623, conclusions on p. 804, pp. 803, col. 2, paragraph 4.

* cited by examiner

*Primary Examiner*—Shaojia Anna Jiang
*Assistant Examiner*—Devesh Khare
(74) *Attorney, Agent, or Firm*—Brian Lewis; Pauline Ann Clarke; J. Elin Hartrum

(57) ABSTRACT

Disclosed are novel compounds that are $A_3$ adenosine receptor agonists, useful for treating various disease states, including cancer, cardiac ischemia, leukopenia, and neutropennia.

22 Claims, No Drawings

ADENOSINE $A_3$ RECEPTOR AGONISTS

This is a continuation in part of U.S. patent application Ser. No. 10/212,896, filed on Aug. 5, 2002 now abandoned, which claims priority to U.S. Provisional Patent Application Ser. No. 60/311,069 filed on Aug. 8, 2001 the complete disclosures of which are hereby incorporated by reference.

FIELD OF THE INVENTION

This invention relates to novel adenosine $A_3$ receptor agonists that are useful in the treatment of neurological, cardiac, and other cellular proliferative disorders. The invention also relates to methods for the preparation of such compounds, and to pharmaceutical compositions containing them.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, stimulation of the $A_1$ adenosine receptors shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter. $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148–153). $A_3$ adenosine receptors modulate cell proliferation processes. In particular, compounds that are $A_3$ receptor agonists have utility in the therapeutic and/or prophylactic treatment of cancer, cardiac disease, infertility, kidney disease, and CNS disorders. Additionally, $A_3$ receptor agonists stimulate bone marrow cell proliferation, and thus induce the secretion of G-CSF in the body. Accordingly, $A_3$ receptor agonists are useful for countering the toxic side effect of drugs, in particular chemotherapeutic drugs, such as leukopenia and neutropenia.

Few ligands for the $A_3$ adenosine receptor have been reported. Some non-selective $N^6$-substituted adenosine derivatives have been described as agonists for the $A_3$ receptor, including APNEA ($N^6$-2-(4-aminophenyl)ethyladenosine), which has been used successfully as a radioligand in its iodinated form (Zhou et al.). Typical xanthine and nonxanthine $A_1$ and $A_2$ receptor antagonists, however, do not appear to bind to this receptor (Zhou et al.).

Accordingly, it is desired to provide compounds that are $A_3$ receptor agonists. Preferably, the compounds would be selective for the $A_3$ receptor, thus avoiding side effects caused by interaction with other adenosine receptors.

SUMMARY OF THE INVENTION

It is an object of this invention to provide $A_3$ receptor agonists. Accordingly, in a first aspect, the invention relates to compounds of Formula I:

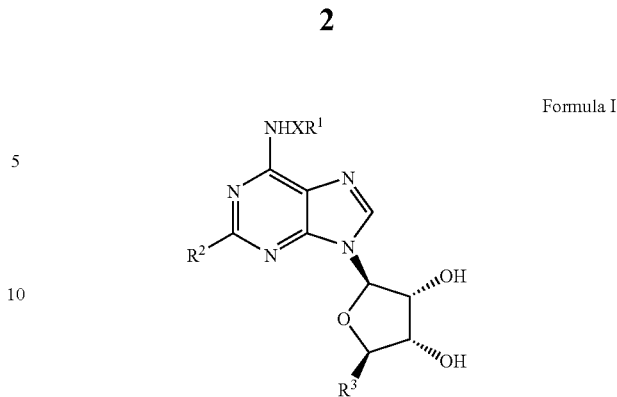

wherein:
$R^1$ is optionally substituted lower alkyl, optionally substituted cycloalkyl, optionally substituted aryl, or optionally substituted heteroaryl;
X is a covalent bond or optionally substituted alkylene;
$R^2$ is $R^4$-Z-Y—C≡C— or optionally substituted pyrazolyl:
in which Y is optionally substituted alkylene, Z is oxygen, sulfur or —NH—, and $R^4$ is
optionally substituted aryl or optionally substituted heteroaryl; and
$R^3$ is hydroxymethyl or —C(O)—$NR^5R^6$;
in which $R^5$ and $R^6$ are independently hydrogen or lower alkyl;

and the pharmaceutically acceptable salts, esters and prodrugs thereof.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be usefully treated with an $A_3$ receptor agonist, comprising administering to a mammal in need thereof a therapeutically effective dose of a compound of Formula I. Such diseases include, but are not limited to, cancer, renal and cardiac ischemia, neurodegenerative disorders, infertility, neutropenia, kidney disease, and CNS disorders.

A fourth aspect of this invention relates to methods of preparing the compounds of Formula I.

Of the compounds of Formula I, one preferred class includes those in which $R^2$ is optionally substituted pyrazol-1-yl, especially where $R^1$ is optionally substituted alkyl or optionally substituted aryl, $R^3$ is hydroxymethyl, and X is a covalent bond. Of these compounds, one preferred group includes those compounds in which $R^2$ is pyrazol-1-yl substituted by optionally substituted lower alkyl, ester, aminocarbonyl, optionally substituted aryl, or optionally substituted heteroaryl.

A preferred subgroup includes those compounds in which $R^2$ is pyrazol-1-yl substituted by optionally substituted phenyl or optionally substituted alkyl, and $R^1$ is optionally substituted alkyl. More preferred are those compounds in which $R^1$ is lower alkyl of 1–3 carbon atoms and $R^2$ is pyrazol-1-yl substituted by phenyl or benzyl having methoxy or chloro substitutions.

A second preferred subgroup includes those compounds in which $R^2$ is pyrazol-1-yl substituted by optionally substituted heteroaryl and $R^1$ is optionally substituted alkyl.

More preferred are those compounds in which $R^1$ is lower alkyl of 1–3 carbon atoms and $R^2$ is pyrazol-1-yl substituted by pyridine.

A third preferred subgroup includes those compounds in which $R^2$ is pyrazol-1-yl substituted by optionally substituted phenyl, $R^1$ is optionally substituted phenyl, and X is alkylene. More preferred are those compounds in which $R^1$ is 3-iodophenyl, especially where X is methylene.

A second preferred class includes compounds in which $R^2$ is pyrazol-4-yl optionally substituted by optionally substituted phenyl or optionally substituted alkyl, especially where $R^1$ is optionally substituted alkyl and X is a covalent bond. More preferred are those compounds in which $R^1$ is lower alkyl.

A third preferred class includes those compounds in which $R^2$ is $R^4$-Z-Y—C≡C—, especially where $R^4$ is optionally substituted phenyl and Y is alkylene of 1, 2, or 3 carbon atoms. Of these compounds, a preferred group includes those compounds in which $R^4$ is phenyl optionally substituted by methoxy or chloro, and Y is methylene, $R^1$ is optionally substituted lower alkyl, $R^3$ is hydroxy, X is a covalent bond, and Z is oxygen.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl,n-decyl, tetradecyl, and the like.

The term "substituted alkyl" refers to:
1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
2) an alkyl group as defined above that is interrupted by 1–10 atoms independently chosen from oxygen, sulfur and $NR_a$—, where $R_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or
3) an alkyl group as defined above that has both 1, 2, 3, 4 or 5 substituents as defined above and is also interrupted by 1–10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, preferably having from 1 to 20 carbon atoms, preferably 1–10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "lower alkylene" refers to a diradical of a branched or unbranched saturated hydrocarbon chain, preferably having from 1, 2, 3, 4, 5, or 6 carbon atoms.

The term "substituted alkylene" refers to:
(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
(2) an alkylene group as defined above that is interrupted by 1–20 atoms independently chosen from oxygen, sulfur and $NR_a$—, where $R_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both 1, 2, 3, 4 or 5 substituents as defined above and is also interrupted by 1–20 atoms as defined above. Examples of substituted alkylenes are chloromethylene (—CH(Cl)—), aminoethylene (—CH($NH_2$)$CH_2$—), methylaminoethylene (—CH(NHMe)$CH_2$—), 2-carboxypropylene isomers(—$CH_2$CH($CO_2$H)$CH_2$—), ethoxyethyl (—$CH_2CH_2$O—$CH_2CH_2$—), ethylmethylaminoethyl (—$CH_2CH_2$N($CH_3$)$CH_2CH_2$—), 1-ethoxy-2-(2-ethoxy-ethoxy)ethane (—$CH_2CH_2$O—$CH_2CH_2$—$OCH_2CH_2$—$OCH_2CH_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloaklyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$R$_a$, in which R$_a$ is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with 1, 2, 3, 4 or 5 substituents, preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

One choice for the definition of $R^4$ in Formula I is a heteroaryl, namely an optionally substituted pyrazole. This definition is intended to include pyrazoles attached:

a) through the N1 position of the pyrazole, that is a pyrazol-1-yl moiety of the formula:

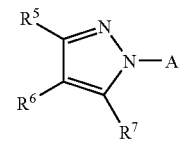

in which A represents the point of attachment to the 2-position of the compound of Formula I, and $R^5$, $R^6$, and $R^7$ are independently hydrogen or those optional substitutions shown for heteroaryl above; and b) through any carbon atom of the pyrazole, that is a C-pyrazolyl of the formula:

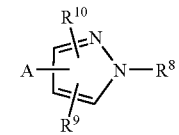

in which A represents the point of attachment to the 2-position of the compound of Formula I, and $R^8$, $R^9$ and, $R^{10}$ are independently hydrogen or those optional substitutions shown for heteroaryl above.

Preferred are optionally substituted pyrazol-1-yl and optionally substituted pyrazol-4-yl. Preferred substitutions are hydrogen, optionally substituted aryl, optionally substituted aralkyl, optionally substituted heteroaryl, and optionally substituted heteroaralkyl.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2R$, in which R is alkyl, aryl, or heteroaryl. "Substituted sulfone" refers to a group —$S(O)_2R$, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is methyl, $R^2$ is 4-(4-methoxyphenyl)pyrazol-1-yl, $R^3$ is hydroxymethyl, and X is a covalent bond:

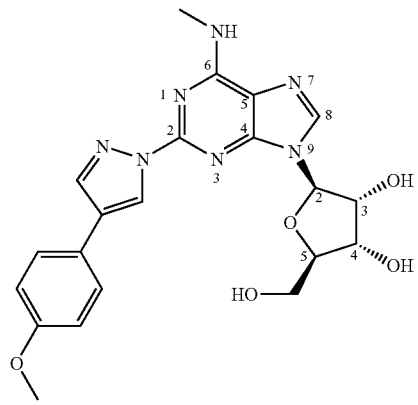

which is named:
(4S,2R,3R,5R)-5-(hydroxymethyl)-2-{2-[4-(4-methoxyphenyl)pyrazolyl]-6-(methylamino)purin-9-yl}oxolane-3,4-diol Synthesis of the Compounds of Formula I An example of a method for preparing the compounds of Formula I where $R^2$ is optionally substituted pyrazol-1-yl is shown in Reaction Scheme I.

REACTION SCHEME I

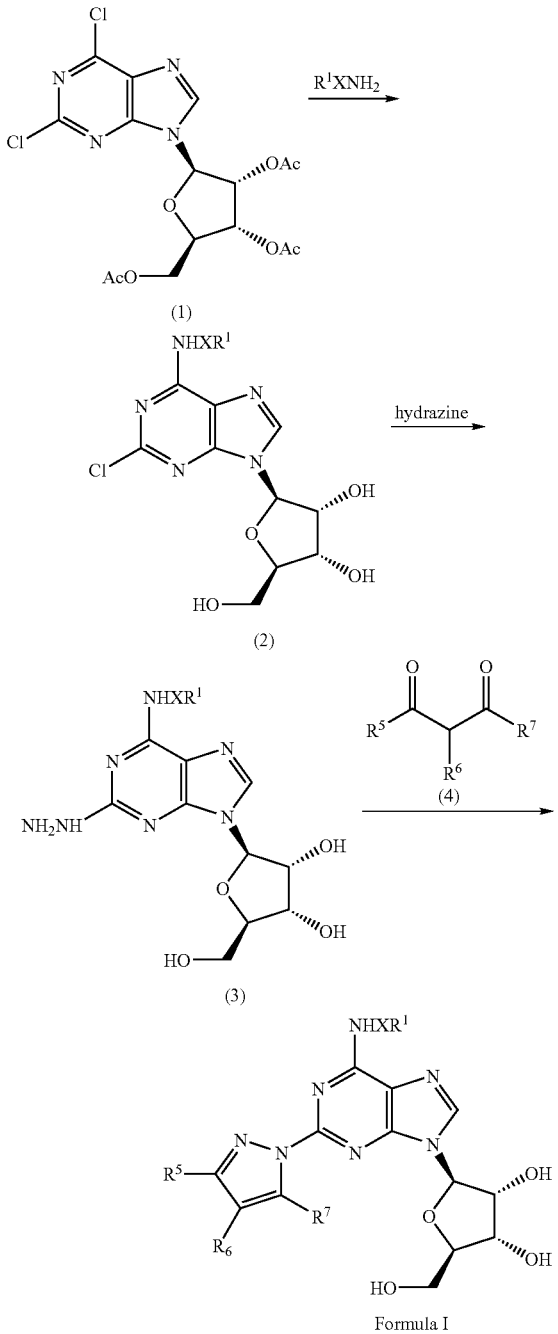

where Ac is acetyl, and X is a covalent bond or optionally substituted alkylene.

Step 1—Preparation of Formula (2)

The compound of formula (2) is prepared by displacement of the 6-chloro of a compound of formula (1), which is prepared as described in J. F. Gorster and R. K. Robins, J. Org. Chem. 1966, Vol. 31, 3258–62. The compound of formula (1) is reacted with a compound of formula $R^1XNH_2$, where X is a covalent bond or optionally substituted alkylene, in the presence of a base. The reaction is carried out in an inert protic solvent, for example methanol, ethanol, n-butanol, and the like, at a temperature of between room temperature and about reflux, for about 12–48 hours. When the reaction is substantially complete, the product of formula (2) is isolated by conventional means, for example by removal of the solvent under reduced pressure, followed by chromatography of the residue on silica gel.

Step 2—Preparation of Formula (3)

The compound of formula (2) is converted to a compound of formula (3) by reaction with hydrazine hydrate. The reaction is carried out with no solvent, or optionally in a protic solvent, for example ethanol, at a temperature of between room temperature and about reflux, for about 12–48 hours. When the reaction is substantially complete, the product of formula (3) is isolated by conventional means, for example by removal of solvent under reduced pressure and triturating the product with ether. Alternatively, the compound of Formula (3) is used in the next step without purification.

Step 3—Preparation of Formula I

The compound of formula (3) is converted to a compound of Formula I by reaction with an optionally substituted 1,3-propanedione derivative of formula (4). The reaction is carried out by suspending the compound of formula (3) in a protic solvent, preferably ethanol, adding the compound of formula (4), and refluxing the mixture for about 2–16 hours. When the reaction is substantially complete, the product of Formula I is isolated by conventional means, for example filtering off the product.

For example, starting with a compound of formula (4) in which $R^5$ and $R^7$ are hydrogen and $R^6$ is 4-methoxyphenyl provides a compound of Formula I in which $R^2$ is 4-methoxyphenylpyrazol-1-yl. Starting with a compound of formula (4) in which $R^5$ and $R^7$ are hydrogen and $R^6$ is —$CO_2Et$ provides a compound of Formula I in which $R^2$ is 4-ethoxycarbonylpyrazol-1-yl. This ester group can then be hydrolyzed under basic conditions to give the free acid, which in turn can be converted to acid derivatives such as optionally substituted amide by means well known to those skilled in the art, or by the method shown in Reaction Scheme IA.

REACTION SCHEME IA

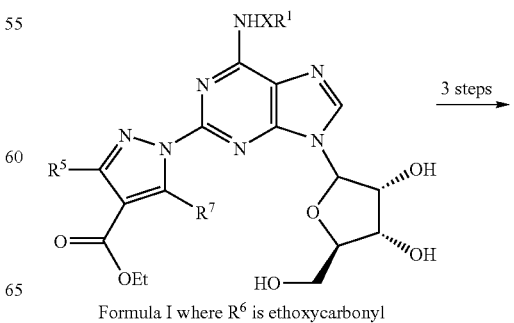

Formula I where $R^6$ is ethoxycarbonyl

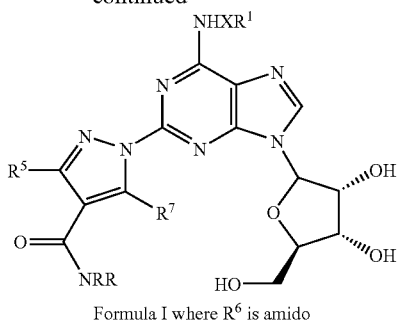

Formula I where R⁶ is amido

Step 1—Protection of the Compound of Formula I where R⁶ is Ethoxycarbonyl

The compound of Formula I in which R⁶ is ethoxycarbonyl is dissolved in a polar solvent, preferably DMF, and imidazole and tertiary butyldimethylsilyl chloride added. The reaction is carried out at a temperature of 50–100° C., for about 12–48 hours. When the reaction is substantially complete, the product is isolated by conventional means, for example by removal of the solvent under reduced pressure, followed by flash chromatography of the residue on silica gel.

Step 2—Hydrolysis of the Ethyl Ester to the Carboxylic Acid

The product from Step 1 is suspended in a mixture of water, an alcohol, and a strong base, preferably potassium hydroxide in methanol. The reaction is carried out at a temperature of 0–40° C., preferably about 25° C., for about 2–5 days, preferably about 3 days. When the reaction is substantially complete, the solvent is removed under reduced pressure, the residue acidified to a pH of about 5, and the product is isolated by conventional means, for example by filtration.

Step 3—Preparation of an Amide

The product from Step 2 is dissolved in an inert solvent, preferably dichloromethane, to which is added HBTU, HOBt, N-methylmorpholine,a catalytic amount of DMAP, and an optionally substituted amine of formula HNRR, as defined above. The reaction is carried out at a temperature of 0–40° C., preferably about 25° C., for about 8–48 hours, preferably about 24 hours. When the reaction is substantially complete, the product is isolated by conventional means.

Step 4—Deprotection

The product from Step 2 is treated with a solution of ammonium fluoride in methanol. The reaction is carried out at a temperature of about reflux, for about 8–48 hours, preferably about 24 hours. When the reaction is substantially complete, the solvent is removed under reduced pressure, the residue acidified to a pH of about 5, and the product is isolated by conventional means, for example by preparative TLC.

A example of a method for preparing the compounds of Formula I where R² is optionally substituted pyrazol-4-yl is shown in Reaction Scheme II. This method and other general methods of preparation of pyrazol-4-yl derivatives are shown in U.S. Pat. No. 6,214,807, the complete disclosure of which is hereby incorporated by reference.

REACTION SCHEME II

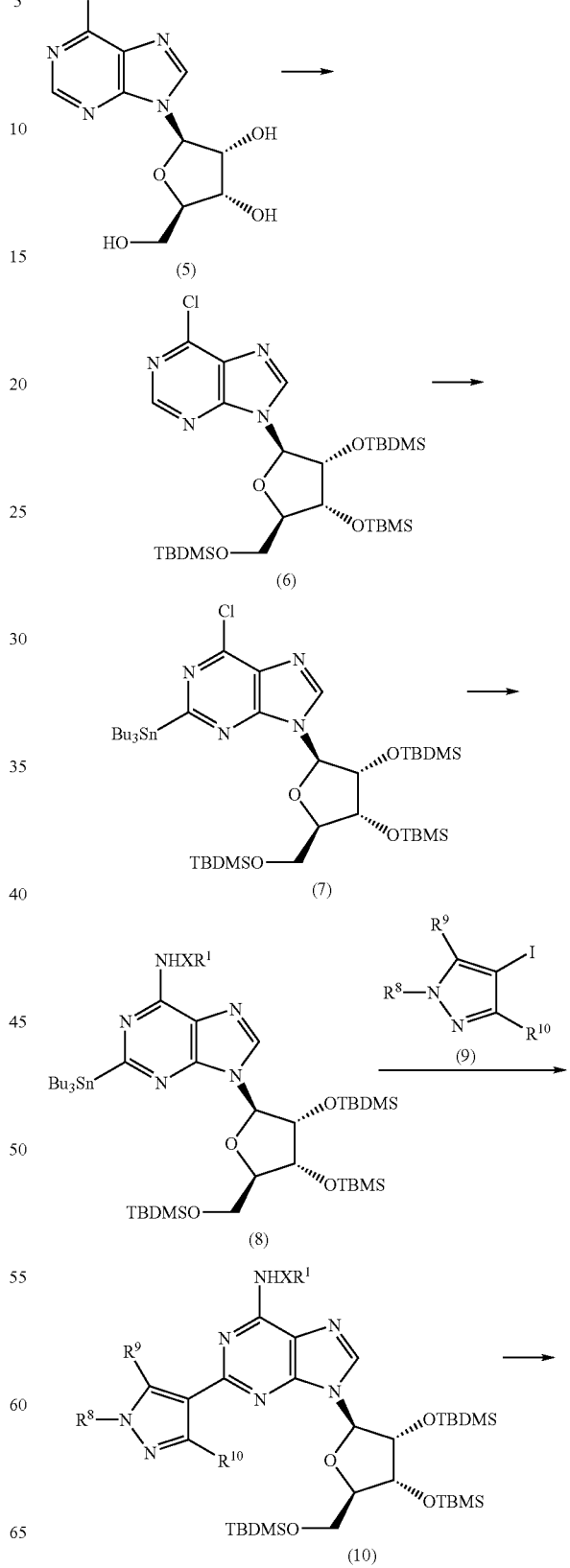

-continued

Formula I

The starting material of formula (5) is prepared by means well know in the art. The intermediate of formula (9) is prepared as shown below.

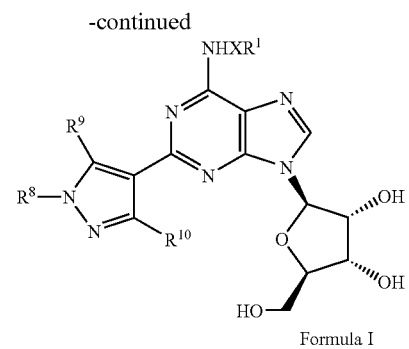

(a) → (b) → (c) → (9)

Condensation of a 1,3-dione of formula (a) with hydrazine in an appropriate solvent provides a pyrazole of formula (b), which is N-alkylated with an appropriate halide of formula $R^8$Hal to give a compound of formula (c). Formation of an anion at the 4-position with a strong base followed by quenching with iodine provides the 4-iodo derivative of formula (9) (F. Effenberger et. al. J. Org. Chem. (1984), 49, 4687).

The iodopyrazole of formula (9) is converted to the corresponding compound of formula (10) by palladium mediated coupling with the compound of formula (8) in the presence or absence of copper salts (K. Kato et. al. J. Org. Chem. 1997, 62, 6833–6841; Palladium Reagents and Catalysts-Innovations in Organic Synthesis, Tsuji, John Wiley and Sons, 1995). The synthesis of the tributyltin derivative of formula (7) has been previously described (K. Kato et. al. J. Org. Chem. 1997, 62, 6833–6841), as shown above in Reaction Scheme II.

An example of a method for preparing the compounds of Formula I where $R^2$ is an ethynyl derivative is shown in Reaction Scheme III.

REACTION SCHEME III (11)

-continued (12)

(13)

Formula I where $R^8$ represents optionally substituted aryl or aralkyl and Z is oxygen, sulfur, or —NH—.

Step 1—Preparation of Formula (12)

The starting compound of formula (11) (2-iodoadenosine) is prepared in four steps from guanosine following literature procedures (M. J. Robins et.al. Can. J. Chem. (1981), 59, 2601–2607; J. F. Cerster et.al. Org. Synthesis, 242–243; V. Nair at. al., J. Org. Chem., (1988), 53, 3051–3057).

The compound of formula (12) is prepared by displacement of the 6-chloro substituent of a compound of formula (11) by reaction with a compound of formula $R^1XNH_2$, where X is a covalent bond or optionally substituted alkylene, in the presence of a base, in the same manner as shown above for the preparation of a compound of formula (2).

Step 2—Preparation of Formula I

The compound of Formula I where $R^2$ is an ethynyl derivative is prepared from a compound of formula (12) by reaction with an appropriately substituted ethynyl derivative of formula (13). The reaction is carried out in a polar solvent, preferably DMF, in the presence of copper iodide and dichlorobis(triphenylphosphine)palladium(II) catalyst, at a temperature of about 50–100° C., preferably in a sealed tube, for about 2–16 hours. When the reaction is substantially complete, the product of Formula I is isolated by conventional means, for example by thin layer chromatography.

Preferred Processes and Last Steps

The compounds of the present invention can be prepared according to the following last steps:

1. Contacting a compound of the formula:

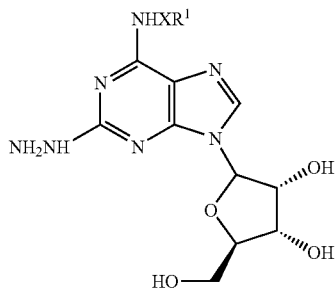
(3)

with a compound of formula:

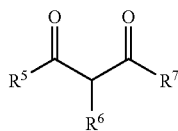
(4)

2. Contacting a compound of the formula:

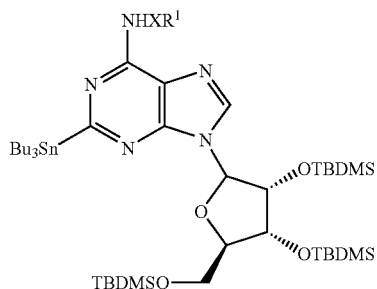
(8)

with a compound of the formula:

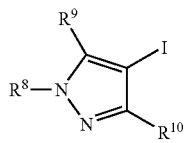
(9)

and contacting the product with a mild acid, for example ammonium fluoride, to remove the protecting groups.

3. Contacting a compound of the formula:

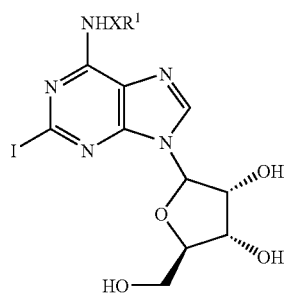
(12)

with a compound of the formula:

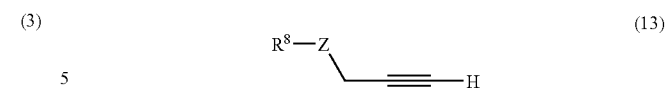
(13)

in the presence of a copper salt and a catalyst.

Utility, Testing and Administration

General Utility

The compounds of Formula I are effective in the treatment of conditions known to respond to administration of $A_3$ adenosine receptor agonists. Such conditions include, but are not limited to, modulation of cell proliferation processes. In particular, compounds that are $A_3$ receptor agonists have utility in the therapeutic and/or prophylactic treatment of cancer, cardiac disease (including use as an ischemia-reperfusion agent), infertility, kidney disease, and CNS disorders. Additionally, they are useful for countering the toxic side effect of drugs, in particular chemotherapeutic drugs, such as leukopenia and neutropenia.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985) and "Modern Pharmaceutics", Marcel Dekker, Inc. 3rd Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention.

Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and are generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

A. Preparation of a Compound of Formula (2) Where $R^1$ is Methyl and X is a Covalent Bond

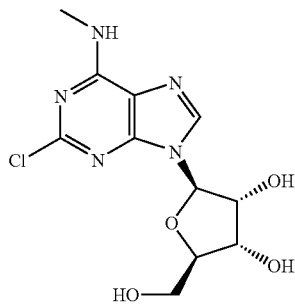

(2)

3,4-diacetyloxy-2-(2,6-dichloropurin-9-yl)-5-(2-oxopropoxy)tetrahydrofuran, the compound of formula (1) (1 mmol), was suspended in a mixture of 1:4 methylamine/MeOH, and the mixture stirred at room temperature for 24 hours. The solvent was removed under reduced pressure and the residue triturated in ether, to afford (4S,2R,3R,5R)-2-[2-chloro-6-(methylamino)purin-9-yl]-5-(hydroxymethyl)oxolane-3,4-diol, a compound of formula (2) as a white solid.

B. Preparation of a Compound of Formula (2), Varying $R^1$ and X

Similarly, following the procedure of 1A above, but replacing methylamine by propylamine and 3-iodobenzylamine, the following compounds of formula (2) were prepared:

(4S,2R,3R,5R)-2-[2-chloro-6-(propylamino)purin-9-yl]-5-(hydroxymethyl)oxolane-3,4-diol; and (4S,2R,3R,5R)-2-[2-chloro-6-(3-iodobenzylamino)purin-9-yl]-5-(hydroxymethyl)oxolane-3,4-diol.

C. Preparation of a Compound of Formula (2), Varying $R^1$ and X

Similarly, following the procedure of 1A above, but replacing methylamine by other compounds of formula $R^1XNH_2$, the following compounds of formula (2) are prepared:

(4S,2R,3R,5R)-2-[2-chloro-6-(ethylamino)purin-9-yl]-5-(hydroxymethyl)oxolane-3,4-diol;

(4S,2R,3R,5R)-2-[2-chloro-6-(n-propylamino)purin-9-yl]-5-(hydroxymethyl)oxolane-3,4-diol;

(4S,2R,3R,5R)-2-[2-chloro-6-(cyclopropylamino)purin-9-yl]-5-(hydroxymethyl)oxolane-3,4-diol;

(4S,2R,3R,5R)-2-[2-chloro-6-(cyclopropylmethylamino)purin-9-yl]-5-(hydroxymethyl)oxolane-3,4-diol;

(4S,2R,3R,5R)-2-[2-chloro-6-(cyclopentylamino)purin-9-yl]-5-(hydroxymethyl)oxolane-3,4-diol;

(4S,2R,3R,5R)-2-[2-chloro-6-(anilinopurin-9-yl)]-5-(hydroxymethyl)oxolane-3,4-diol;

(4S,2R,3R,5R)-2-[2-chloro-6-(4-chlorobenzylamino)purin-9-yl]-5-(hydroxymethyl)oxolane-3,4-diol;

(4S,2R,3R,5R)-2-[2-chloro-6-(benzylamino)purin-9-yl]-5-(hydroxymethyl)oxolane-3,4-diol;

(4S,2R,3R,5R)-2-[2-chloro-6-(2-fluorobenzylamino)purin-9-yl]-5-(hydroxymethyl)oxolane-3,4-diol;

(4S,2R,3R,5R)-2-[2-chloro-6-(pyrid-2-ylamino)purin-9-yl]-5-(hydroxymethyl)oxolane-3,4-diol; and (4S,2R,3R,5R)-2-[2-chloro-6-(pyrrol-3-ylamino)purin-9-yl]-5-(hydroxymethyl)oxolane-3,4-diol.

D. Preparation of a Compound of Formula (2), Varying $R^1$ and X

Similarly, following the procedure of 1A above, but replacing methylamine by other compounds of formula $R^1XNH_2$, other compounds of formula (2) are prepared.

EXAMPLE 2

Preparation of a Compound of Formula (3)

A. Preparation of a Compound of Formula (3) where $R^1$ is Methyl and X is a Covalent Bond

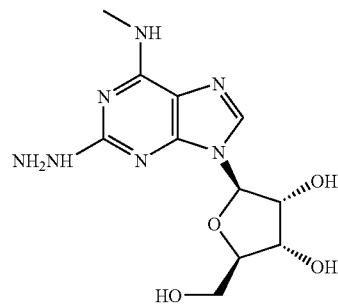

(3)

(4S,2R,3R,5R)-2-[2-chloro-6-(methylamino)purin-9-yl]-5-(hydroxymethyl)oxolane-3,4-diol, a compound of formula (2) (0.5 mmol), was suspended in hydrazine hydrate (5 mL), and the mixture was allowed to stir at room temperature for 24 hours. The hydrazine was removed under reduced pressure and the residue triturated with ether and filtered, to afford (4S,2R,3R,5R)-2-[2-hydrazino-6-(methylamino)purin-9-yl]-5-(hydroxymethyl)oxolane-3,4-diol, a compound of formula (3), as a white solid.

B. Preparation of a Compound of Formula (3), Varying $R^1$ and X

Similarly, following the procedure of 2A above, but replacing 2-(2-chloro-6-methylaminopurin-9-yl)-5-hydroxymethyltetrahydrofuran-3,4-diol by the propylamino and 3-iodobenzylamino anaolgs of formula (2), the following compounds of formula (3) were prepared:

(4S,2R,3R,5R)-2-[2-hydrazino-6-(n-propylamino)purin-9-yl]-5-(hydroxylethyl)oxolane-3,4-diol; and (4S,2R,3R,5R)-2-[2-hydrazino-6-(3-iodobenzylamino)purin-9-yl]-5-(hydroxymethyl)oxolane-3,4-diol.

C. Preparation of a Compound of Formula (3), Varying $R^1$ and X

Similarly, following the procedure of 2A above, but replacing 2-(2-chloro-6-methylaminopurin-9-yl)-5-hydroxymethyltetrahydrofuran-3,4-diol by other compounds of formula (2), the following compounds of formula (3) are prepared:
(4S,2R,3R,5R)-2-[2-hydrazino-6-(ethylamino)purin-9-yl]-5-(hydroxymethyl)oxolane-3,4-diol;
(4S,2R,3R,5R)-2-[2-hydrazino-6-(cyclopropylamino)purin-9-yl]-5-(hydroxymethyl)oxolane-3,4-diol;
(4S,2R,3R,5R)-2-[2-hydrazino-6-(cyclopropylmethylamino)purin-9-yl]-5-(hydroxymethyl)oxolane-3,4-diol;
(4S,2R,3R,5R)-2-[2-hydrazino-6-(cyclopentylamino)purin-9-yl]-5-(hydroxymethyl)oxolane-3,4-diol;
(4S,2R,3R,5R)-2-[2-hydrazino-6-(anilinopurin-9-yl)]-5-(hydroxymethyl)oxolane-3,4-diol;
(4S,2R,3R,5R)-2-[2-hydrazino-6-(4-chlorobenzylamino) purin-9-yl]-5-(hydroxymethyl)oxolane-3,4-diol;
(4S,2R,3R,5R)-2-[2-hydrazino-6-(benzylamino)purin-9-yl]-5-(hydroxymethyl)oxolane-3,4-diol;
(4S,2R,3R,5R)-2-[2-hydrazino-6-(2-fluorobenzylamino)purin-9-yl]-5-(hydroxymethyl)oxolane-3,4-diol;
(4S,2R,3R,5R)-2-[2-hydrazino-6-(pyrid-2-ylamino)purin-9-yl]-5-(hydroxymethyl)oxolane-3,4-diol; and
(4S,2R,3R,5R)-2-[2-hydrazino-6-(pyrrol-3-ylamino)purin-9-yl]-5-(hydroxymethyl)oxolane-3,4-diol.

D. Preparation of a Compound of Formula (3), Varying $R^1$ and X

Similarly, following the procedure of 2A above, but replacing 2-(2-chloro-6-methylaminopurin-9-yl)-5-hydroxymethyltetrahydrofuran-3,4-diol by other compounds of formula (2), other compounds of formula (3) are prepared.

EXAMPLE 3

Preparation of a Compound of Formula I

A. Preparation of a Compound of Formula I where $R^1$ is Methyl, $R^2$ is 4-(4-Methoxyphenyl)pyrazol-1-yl, and X is a Covalent Bond

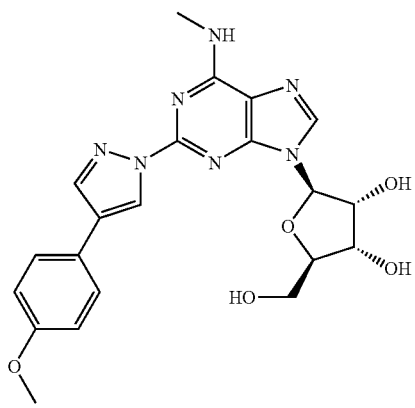

Formula I (4S,2R,3R,5R)-2-[2-hydrazino-6-(methylamino)purin-9-yl]-5-(hydroxymethyl)oxolane-3,4-diol (0.5 mmol) was suspended in 3 mL of ethanol and to the suspension was added 2-(4-methoxyphenyl)malonaldehyde, a compound of formula (4). The mixture was heated at reflux for 5 hours, and the precipitate thus formed was collected by filtration, and washed with ethanol and ether to afford (4S,2R,3R,5R)-5-(hydroxymethyl)-2-{2-[4-(4-methoxyphenyl)pyrazolyl]-6-(methylamino)purin-9-yl}oxolane-3,4-diol, a compound of Formula I, Ms, 455.43 (M+1).

B. Preparation of a Compound of Formula I, Varying $R^1$, $R^2$, and X

Similarly, following the procedure of 3A above, but optionally replacing 2-(2-hydrazino-6-methylaminopurin-9-yl)-5-hydroxymethyltetrahydrofuran-3,4-diol with other compounds of formula (3), and optionally replacing 2-(4-methoxyphenyl)malonaldehyde with other compounds of formula (4), the following compounds of Formula I were prepared:
(4S,2R,3R,5R)-5-(hydroxymethyl)-2-{2-[4-(4-ethoxycarbonyl)pyrazolyl]-6-(methylamino)purin-9-yl}oxolane-3,4-diol;
(4S,2R,3R,5R)-5-(hydroxymethyl)-2-{2-[4-(4-ethoxycarbonyl)pyrazolyl]-6-(n-propylamino)purin-9-yl}oxolane-3,4-diol;
(4S,2R,3R,5R)-5-(hydroxymethyl)-2-{2-[4-(4-ethoxycarbonyl)pyrazolyl]-6-(3-iodobenzylamino)purin-9-yl}oxolane-3,4-diol;
(4S,2R,3R,5R)-5-(hydroxymethyl)-2-{2-[4-(3-ethoxycarbonyl)pyrazolyl]-6-(methylamino)purin-9-yl}oxolane-3,4-diol;
(4S,2R,3R,5R)-5-(hydroxymethyl)-2-{2-[4-(4-ethoxycarbonyl)pyrazolyl]-6-(methylamino)purin-9-yl}oxolane-3,4-diol;
(4S,2R,3R,5R)-5-(hydroxymethyl)-2-{2-[4-(3-ethoxycarbonyl)pyrazolyl]-6-(3-iodobenzylamino)purin-9-yl}oxolane-3,4-diol;
(4S,2R,3R,5R)-5-(hydroxymethyl)-2-{2-[4-(amido)pyrazolyl]-6-(methylamino)purin-9-yl}oxolane-3,4-diol;
(4S,2R,3R,5R)-5-(hydroxymethyl)-2-{2-[4-(methylamido)pyrazolyl]-6-(n-propylamino)purin-9-yl}oxolane-3,4-diol;
(4S,2R,3R,5R)-5-(hydroxymethyl)-2-{2-[4-(ethylamido)pyrazolyl]-6-(3-iodobenzylamino)purin-9-yl}oxolane-3,4-diol;
(4S,2R,3R,5R)-5-(hydroxymethyl)-2-{2-[4-(propylamido)pyrazolyl]-6-(3-iodobenzylamino)purin-9-yl}oxolane-3,4-diol;
(4S,2R,3R,5R)-5-(hydroxymethyl)-2-{2-[4-(cyclopentylamido)pyrazolyl]-6-(3-iodobenzylamino)purin-9-yl}oxolane-3,4-diol;
(4S,2R,3R,5R)-5-(hydroxymethyl)-2-{2-[4-(ethylamido)pyrazolyl]-6-(3-iodobenzylamino)purin-9-yl}oxolane-3,4-diol;
(4S,2R,3R,5R)-5-(hydroxymethyl)-2-{2-[4-(4-methylphenyl)pyrazolyl]-6-(methylamino)purin-9-yl}oxolane-3,4-diol;
(4S,2R,3R,5R)-5-(hydroxymethyl)-2-{2-[4-(4-methylphenyl)pyrazolyl]-6-(cyclopentylamino)purin-9-yl}oxolane-3,4-diol;
(4S,2R,3R,5R)-5-(hydroxymethyl)-2-{2-[4-(4-methoxyphenyl)pyrazolyl]-6-(n-propylamino)purin-9-yl}oxolane-3,4-diol;
(4S,2R,3R,5R)-5-(hydroxymethyl)-2-{2-[4-(4-methoxyphenyl)pyrazolyl]-6-(3-iodobenzylamino)purin-9-yl}oxolane-3,4-diol;
(4S,2R,3R,5R)-5-(hydroxymethyl)-2-{2-[4-(4-chlorophenyl)pyrazolyl]-6-(3-iodobenzylamino)purin-9-yl}oxolane-3,4-diol;
(4S,2R,3R,5R)-5-(hydroxymethyl)-2-[4-(pyrimidin-5-yl) pyrazolyl]-6-(methylamino)purin-9-yl}oxolane-3,4-diol;
(4S,2R,3R,5R)-5-(hydroxymethyl)-2-[4-(pyrimidin-5-yl) pyrazolyl]-6-(3-iodobenzylamino)purin-9-yl}oxolane-3,4-diol;

(4S,2R,3R,5R)-5-(hydroxymethyl)-2-[4-(pyridin-2-yl)pyrazolyl]-6-(n-propylamino)purin-9-yl}oxolane-3,4-diol;

(4S,2R,3R,5R)-5-(hydroxyethyl)-2-[4-(pyridin-2-yl)pyrazolyl]-6-(3-iodobenzylamino)purin-9-yl}oxolane-3,4-diol;

(4S,2R,3R,5R)-5-(hydroxymethyl)-2-[4-(pyridin-4-yl)pyrazolyl]-6-(methylamino)purin-9-yl}oxolane-3,4-diol;

(4S,2R,3R,5R)-5-(hydroxymethyl)-2-[4-(pyridin-4-yl)pyrazolyl]-6-(3-iodobenzylamino)purin-9-yl}oxolane-3,4-diol;

(4S,2R,3R,5R)-5-(hydroxymethyl)-2-[4-(pyridin-2-yl)pyrazolyl]-6-(methylamino)purin-9-yl}oxolane-3,4-diol;

(4S,2R,3R,5R)-5-(hydroxymethyl)-2-[4-(benzoxazol-2-yl)pyrazolyl]-6-(methylamino)purin-9-yl}oxolane-3,4-diol;

(4S,2R,3R,5R)-5-(hydroxymethyl)-2-[4-(benzoxazol-2-yl)pyrazolyl]-6-(3-iodobenzylamino)purin-9-yl}oxolane-3,4-diol;

(4S,2R,3R,5R)-5-(hydroxymethyl)-2-[4-(pyridin-2-yl)pyrazolyl]-6-(methylamino)purin-9-yl}oxolane-3,4-diol;

(4S,2R,3R,5R)-5-(hydroxymethyl)-2-[4-(quinolin-2-yl)pyrazolyl]-6-(3-methylamino)purin-9-yl}oxolane-3,4-diol;

(4S,2R,3R,5R)-5-(hydroxymethyl)-2-[4-(isoquinolin-1-yl)pyrazolyl]-6-(3-iodobenzylamino)purin-9-yl}oxolane-3,4-diol;

(4S,2R,3R,5R)-5-(hydroxymethyl)-2-{2-[3,5-dimethylpyrazolyl]-6-(methylamino)purin-9-yl}oxolane-3,4-diol;

(4S,2R,3R,5R)-5-(hydroxymethyl)-2-{2-[4-n-butyl-3,5-dimethylpyrazolyl]-6-(methylamino)purin-9-yl}oxolane-3,4-diol; and (4S,2R,3R,5R)-5-(hydroxymethyl)-2-{2-[4-n-propyl-3,5-dimethylpyrazolyl]-6-(methylamino)purin-9-yl}oxolane-3,4-diol.

C. Preparation of a Compound of Formula I, Varying $R^1$, $R^2$, and X

Similarly, following the procedure of 3A above, but optionally replacing 2-(2-hydrazino-6-methylaminopurin-9-yl)-5-hydroxymethyltetrahydrofuran-3,4-diol with other compounds of formula (3), and optionally replacing 2-(4-methoxyphenyl)malonaldehyde with other compounds of formula (4), the following compounds of Formula I are prepared:

(4S,2R,3R,5R)-5-(hydroxymethyl)-2-{2-[4-(4-methoxyphenyl)pyrazolyl]-6-(ethylamino)purin-9-yl}oxolane-3,4-diol;

(4S,2R,3R,5R)-5-(hydroxymethyl)-2-{2-[4-ethoxycarbonyl)pyrazolyl]-6-(ethylamino)purin-9-yl}oxolane-3,4-diol;

(4S,2R,3R,5R)-5-(hydroxymethyl)-2-{2-[4-(4-methoxyphenyl)pyrazolyl]-6-(n-propylamino)purin-9-yl}oxolane-3,4-diol;

(4S,2R,3R,5R)-5-(hydroxymethyl)-2-{2-[4-(4-methoxyphenyl)pyrazolyl]-6-(cyclopropylamino)purin-9-yl}oxolane-3,4-diol;

(4S,2R,3R,5R)-5-(hydroxymethyl)-2-{2-[4-(4-methoxyphenyl)pyrazolyl]-6-(cyclopropylmethylamino)purin-9-yl}oxolane-3,4-diol;

(4S,2R,3R,5R)-5-(hydroxymethyl)-2-{2-[4-propylamido)pyrazolyl]-6-(cyclopropylamino)purin-9-yl}oxolane-3,4-diol;

(4S,2R,3R,5R)-5-(hydroxymethyl)-2-{2-[4-(4-methoxyphenyl)pyrazolyl]-6-(anilinopurin-9-yl}oxolane-3,4-diol;

(4S,2R,3R,5R)-5-(hydroxymethyl)-2-{2-[pyridin-4-yl]pyrazolyl]-6-(3-iodobenzylamino)purin-9-yl}oxolane-3,4-diol;

(4S,2R,3R,5R)-5-(hydroxymethyl)-2-{2-[4-(4-methoxyphenyl)pyrazolyl]-6-(benzylamino)purin-9-yl}oxolane-3,4-diol;

(4S,2R,3R,5R)-5-(hydroxymethyl)-2-{2-[4-(4-methoxyphenyl)pyrazolyl]-6-(2-fluorobenzylamino)purin-9-yl}oxolane-3,4-diol;

(4S,2R,3R,5R)-5-(hydroxymethyl)-2-{2-[4-(4-methoxyphenyl)pyrazolyl]-6-(pyrid-2-ylamino)purin-9-yl}oxolane-3,4-diol; and (4S,2R,3R,5R)-5-(hydroxymethyl)-2-{2-[4-(4-methoxyphenyl)pyrazolyl]-6-(pyrrol-3-ylmethylamino)purin-9-yl}oxolane-3,4-diol.

D. Preparation of a Compound of Formula I, Varying $R^1$ $R^2$, and X

Similarly, following the procedure of 3A above, but optionally replacing 2-(2-hydrazino-6-methylaminopurin-9-yl)-5-hydroxymethyltetrahydrofuran-3,4-diol with other compounds of formula (3), and optionally replacing 2-(4-methoxyphenyl)malonaldehyde with other compounds of formula (4), other compounds of Formula I are prepared:

EXAMPLE 4

Preparation of a Compound of Formula (12)

A. Preparation of a Compound of Formula (12) where $R^1$ is Methyl

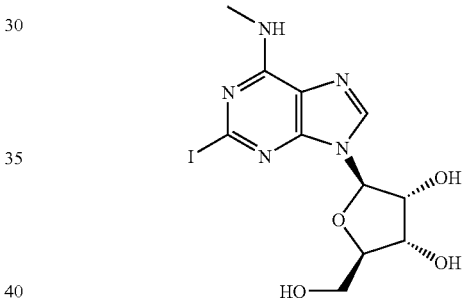

A mixture of 40% aqueous methylamine (1 mL) and 2-iodoadenosine (100 mg) in methanol (2 mL) was stirred at room temperature for 12 hours. The precipitate was filtered off, washed with ether and dried under vacuum to afford 2-iodo-6-methylamino adenosine, a compound of formula (11).

B. Preparation of a Compound of Formula (12), Varying $R^1$

Similarly, following the procedure of 4A above, but replacing methylamine with other amines of formula $R^1NH_2$, the following compounds of formula (11) were prepared:

2-iodo-6-n-propylamino adenosine; and
2-iodo-6-(3-iodobenzyl)amino adenosine.

C. Preparation of a Compound of Formula (12), Varying $R^1$

Similarly, following the procedure of 4A above, but replacing methylamine with other amines of formula HNRR, the following compounds of formula (11) are prepared:

2-iodo-6-ethylamino adenosine;
2-iodo-6-isopropylamino adenosine;
2-iodo-6-n-hexylamino adenosine;
2-iodo-6-cyclopropylamino adenosine;
2-iodo-6-cyclopentylamino adenosine;
2-iodo-6-(3-hydroxycyclopentyl)amino adenosine;

2-iodo-6-cyclopentylmethylamino adenosine;
2-iodo-6-phenylamino adenosine;
2-iodo-6-benzylamino adenosine;
2-iodo-6-(4-methoxybenzyl)amino adenosine;
2-iodo-6-(4-fluorobenzyl)amino adenosine;
2-iodo-6-(pyridy-3-yl)amino adenosine; and
2-iodo-6-(furan-2-yl)amino adenosine.

D. Preparation of a Compound of Formula (12), Varying $R^1$

Similarly, following the procedure of 4A above, but replacing methylamine with other amines of formula HNRR, other compounds of formula (11) are prepared.

EXAMPLE 5

Preparation of a Compound of Formula I

A. Preparation of a Compound of Formula I where $R^1$ is Methyl, $R^2$ is 3-phenoxypropyn-1-yl, and $R^8$ is Phenyl

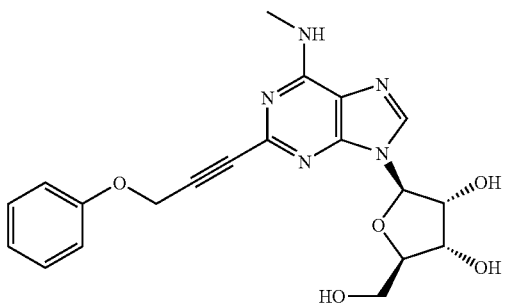

To a solution of 2-iodo-6-methylamino adenosine (50 mg) and prop-2-ynyloxybenzene (0.022 mL, 0.16 mmol) in N,N-dimethylformamide (1 ml) and triethylamine (0.021 mL, 0.16 mmol) at 23 C was added copper iodide (5 mg, 0.026 mmol) and dichlorobis-(triphenylphosphine)palladium(II) (22 mg, 0.031 mmol) catalyst. After being stirred in a sealed reaction-vial at 80° C. for 6 hours, the reaction was concentrated in vacuo, and the residue purified by preparatory thin layer chromatography (methylene chloride:methanol 9:1) to afford (4S,2R,3R,5R)-5-(hydroxymethyl)-2-[6-(methylamino)-2-(3-phenoxyprop-1-ynyl)purin-9-yl]oxolane-3,4-diol, a compound of Formula I. MS: 412.1 (M+1).

B. Preparation of a Compound of Formula I, Varying $R^2$

Similarly, following the procedure of 5A above, but replacing prop-2-ynyloxybenzene with other compounds of formula (7), the following compounds of Formula I were prepared:
(4S,2R,3R,5R)-5-(hydroxymethyl)-2-[2-(3-hydroxy-3-phenylprop-1-ynyl)-6-(methylamino)purin-9-yl]oxolane-3,4-diol;
(4S,2R,3R,5R)-2-{2-[3-(4-chlorophenoxy)prop-1-ynyl]-6-(methylamino)purin-9-yl}-5-(hydroxymethyl)oxolane-3,4-diol; and
(4S,2R,3R,5R)-2-{2-[3-(2-methoxyphenoxy)prop-1-ynyl]-6-(methylamino)purin-9-yl}-5-(hydroxymethyl)oxolane-3,4-diol.

C. Preparation of a Compound of Formula I, Varying $R^1$, $R^2$, and X

Similarly, following the procedure of 5A above, but replacing prop-2-ynyloxybenzene with other compounds of formula (7), the following compounds of Formula I are prepared:

(4S,2R,3R,5R)-5-(hydroxymethyl)-2-[6-(ethylamino)-2-(3-phenoxyprop-1-ynyl)purin-9-yl]oxolane-3,4-diol;
(4S,2R,3R,5R)-5-(hydroxymethyl)-2-[6-(n-propylamino)-2-(3-phenoxyprop-1-ynyl)purin-9-yl]oxolane-3,4-diol;
(4S,2R,3R,5R)-5-(hydroxymethyl)-2-[6-(isopropylamino)-2-(3-phenoxyprop-1-ynyl)purin-9-yl]oxolane-3,4-diol;
(4S,2R,3R,5R)-5-(hydroxymethyl)-2-[6-(n-hexylamino)-2-(3-phenoxyprop-1-ynyl)purin-9-yl]oxolane-3,4-diol;
(4S,2R,3R,5R)-5-(hydroxymethyl)-2-[6-(cyclopropylamino)-2-(3-phenoxyprop-1-ynyl)purin-9-yl]oxolane-3,4-diol;
(4S,2R,3R,5R)-5-(hydroxymethyl)-2-[6-(cyclopentylamino)-2-(3-phenoxyprop-1-ynyl)purin-9-yl]oxolane-3,4-diol;
(4S,2R,3R,5R)-5-(hydroxymethyl)-2-[6-(3-hydroxycyclopentylamino)-2-(3-phenoxyprop-1-ynyl)purin-9-yl]oxolane-3,4-diol;
(4S,2R,3R,5R)-5-(hydroxymethyl)-2-[6-(cyclopentylmethylamino)-2-(3-phenoxyprop-1-ynyl)purin-9-yl]oxolane-3,4-diol;
(4S,2R,3R,5R)-5-(hydroxymethyl)-2-[6-(phenylamino)-2-(3-phenoxyprop-1-ynyl)purin-9-yl]oxolane-3,4-diol;
(4S,2R,3R,5R)-5-(hydroxymethyl)-2-[6-(benzylamino)-2-(3-phenoxyprop-1-ynyl)purin-9-yl]oxolane-3,4-diol;
(4S,2R,3R,1R)-5-(hydroxymethyl)-2-[6-(4-methoxybenzylamino)-2-(3-phenoxyprop-1-ynyl)purin-9-yl]oxolane-3,4-diol;
(4S,2R,3R,1R)-5-(hydroxymethyl)-2-[6-(4-fluorobenzylamino)-2-(3-phenoxyprop-1-ynyl)purin-9-yl]oxolane-3,4-diol;
(4S,2R,3R,5R)-5-(hydroxymethyl)-2-[6-(pyrid-3-ylamino)-2-(3-phenoxyprop-1-ynyl)purin-9-yl]oxolane-3,4-diol; and
(4S,2R,3R,5R)-5-(hydroxymethyl)-2-[6-(furan-2-ylamino)-2-(3-phenoxyprop-1-ynyl)purin-9-yl]oxolane-3,4-diol.

D. Preparation of a Compound of Formula I, Varying $R^1$, $R^2$, and X

Similarly, following the procedure of 5A above, but replacing prop-2-ynyloxybenzene with other compounds of formula (7), other compounds of Formula I are prepared.

EXAMPLE 6

Following the procedures shown in Reaction Scheme II above, as detailed in U.S. Pat. No. 6,214,807, the following compounds of Formula I in which $R^2$ is an optionally substituted C-pyrazole were made:
(1-{9-[(4S,2R,3R,5R)-3,4-dihydroxy-5-(hydroxymethyl)oxolan-2-yl]-6-(methylamino)purin-2-yl}pyrazol-4-yl)-N-(4-chlorophenyl)carboxamide;
(4S,2R,3R,5R)-5-(hydroxymethyl)-2-{2-[1-benzylpyrazol-4-yl]-6-(methylamino)purin-9-yl}oxolane-3,4-diol;
(4S,2R,3R,5R)-5-(hydroxymethyl)-2-{2-[1-benzylpyrazol-4-yl]-6-(n-propylamino)purin-9-yl}oxolane-3,4-diol;
(4S,2R,3R,5R)-5-(hydroxymethyl)-2-{2-[1-benzylpyrazol-4-yl]-6-(3-iodophenylamino)purin-9-yl}oxolane-3,4-diol;

The following examples illustrate the preparation of representative pharmaceutical formulations containing a compound of Formula I, such as those prepared in accordance with Example 1.

EXAMPLE 7

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 8

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 9

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 10

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 11

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 12

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 13

A subcutaneous formulation may be prepared as follows:

| Ingredient | Quantity |
|---|---|
| Active Ingredient | 5.0 mg |
| Corn Oil | 1.0 mL |

EXAMPLE 14

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 15

A topical preparation is prepared having the following composition:

| Ingredients | grams |
| --- | --- |
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C with stirring. A sufficient quantity of water at 60° C is then added with vigorous stirring to emulsify the ingredients, and water then added q.s. 100 g.

EXAMPLE 16

Sustained Release Composition

| Ingredient | Weight Range (%) | Preferred Range (%) | Most Preferred |
| --- | --- | --- | --- |
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Abbreviations

Gpp(NH)p: 5'-guanylyl-imididodiphosphate
R-PIA: phenylisopropyladenosine
TEM buffer: Buffer containing 50 mM Tris, 1 mM EDTA and 10 mM MgCl2

Reagents

Adenosine deaminase is purchased from Boehringer Mannheim Biochemicals Indianapolis, Ind.). R-PIA, DMSO and rolipram are obtained from Sigma-RBI (Natick, Mass.).

EXAMPLE 18

Stable transfection of HEK-293 or CHO cells. The cDNAs for human $A_1$, $A_{2A}$, $A_{2B}$ or $A_3$ adenosine receptors (AdoRs) were prepared by RT-PCR from total RNAs of human cells or tissues and sequenced on both strands. The expression vector containing one of these cDNAs and a second vector containing a neomycin or puromycin-resistance gene were introduced to HEK-293 or CHO cells by Lipofectin-Plus (Life Technology). Colonies were selected by growing transfected cells in the presence of neomycin or puromycin. Stably transfected cells were maintained in Dulbecco's modified Eagle's medium (DMEM) or F-12 medium with 10% fetal bovine serum, 100 µg/mL penicillin, 100 µg/mL streptomycin and appropriate concentrations of neomycin or puromycin. The HEK-$A_{2A}$, HEK-$A_{2B}$ and HEK-$A_3$ cells contain high densities of $A_{2A}$, $A_{2B}$ and $A_3$ AdoRs, respectively. CHO-$A_1$ and CHO-$A_3$ cells contain high densities of $A_1$ and $A_3$ AdoRs, respectively.

Membrane preparation. Monolayers of transfected cells were washed with phosphate buffered saline (PBS) and harvested in a buffer containing 10 mM HEPES (pH 7.4), 10 mM EDTA and protease inhibitors. The cells were homogenized in polytron for 1 minute at setting 4 and centrifuged at 29000 g for 15 minutes at 4° C. The cell pellets were washed with a buffer containing 10 mM HEPES (pH7.4), 1 mM EDTA and protease inhibitors, and were resuspended in the same buffer supplemented with 10% sucrose. Frozen aliquots were kept at −80° C.

Radioligand binding. The affinities of compounds for $A_1$, $A_{2A}$, $A_{2B}$ or $A_3$ AdoRs were determined in competition studies using radioligands such as $^3$H-CPX ($A_1$ antagonist), or $^3$H-CCPA ($A_1$ agonist), $^3$H-ZM 241385 ($A_{2A}$ antagonist) or $^3$H-CGS 21680 ($A_{2A}$ agonist), $^3$H-ZM 241385 ($A_{2B}$ antagonist) or $^{125}$I-AB-MECA ($A_3$ agonist) and membranes of corresponding transfected cells. For example, to determine the affinities for $A_3$ AdoRs, the competition assays were started by mixing 0.2 nM $^{125}$I-AB-MECA with various concentrations of test compounds and 25 µg membrane proteins of HEK-$A_3$ or CHO-$A_3$ in TEM buffer (50 mM Tris, 1 mM EDTA and 10 mM MgCl$_2$) supplemented with 1 U/mL adenosine deaminase. The assays were incubated for 90 minutes, stopped by filtration onto GF/B filter plates using Packard Harvester and washed four times with ice-cold TM buffer (10 mM Tris, 1 mM Mg Cl$_2$, pH 7.4). The amounts of radioligands that bound to the GF/B filter plates were determined by scintillation counting. Nonspecific binding was determined in the presence of 10 μM R-PIA or 1 μM IB-MECA. $B_{max}$ and $K_D$ values were calculated using GraphPad software.

EXAMPLE 19

[$^{35}$S]GTPγS Binding Assays

The ability of the adenosine $A_3$-agonists to stimulate [$^{35}$S] GTPγS binding is determined by a modification of the method described by Lorenzen et al. (1996 Mol. Pharmacol. 49:915). Briefly, membranes isolated from transfected CHO cells (30–50 μg) are incubated in a volume of 0.1 mL containing 50 mM Tris-HCl buffer pH 7.4, 5 mM MgCl$_2$, 100 mM NaCl, 1 mM dithiothreitol, 0.2 units mL$^{-1}$ adenosine deaminase, 0.5% BSA, 1 mM EDTA, various concentrations of GDP and $^{35}$S-GTPγS. Various concentrations of the putative $A_3$ agonists are added and the cells incubated for 5–90 min at 30° C. Nonspecific binding is determined by the addition of high concentrations of GTPγS to some of the membrane suspensions. At the end of the incubation, each suspension is filtered and the retained radioactivity determined as described above.

EXAMPLE 20 cAMP measurements. CHO-$A_3$ or HEK-$A_3$ cells were collected in PBS containing 5 mM EDTA, washed with DMEM and resuspended in DMEM containing adenosine deaminase (1 unit/mL) at a density of 100,000–1,000,000 cells/mL. The cells were kept at room temperature for 0.5–1 hour before the experiments. To start the cAMP measurement, the cell suspension (100 μL) was mixed with 25 μL of test agents and the reaction was kept at 37° C. for 5–30 minutes. The reaction was stopped by addition of 0.2N HCl (125 μL). Cell lysates were centrifuged for 10 minutes at 1000 rpm. The supernatant (100 μL) was collected and acetylated. The concentrations of cAMP in the supernatants were measured using the direct cAMP assay according to the manufacturer's instructions (Assay Design). Alternatively, cells were harvested using 0.0025% trypsin and 2 mM EDTA in PBS, washed and resuspended in phenol-free DMEM to a concentration of 1×10$^6$ cells/mL, and then incubated with 1 U/mL of adenosine deaminase for 30 minutes at room temperature. In some case, a final concentration of 50 μM of the phosphodiesterase IV inhibitor, rolipram, was added to the cells immediately prior to addition of adenosine receptor agonists, antagonists, and forskolin. After incubating for 5–30 minutes at 37° C., cells were lysed and cAMP concentrations were determined using cAMP-Screen Direct™ System (Applied Biosystem) according to the manufacturer's instructions.

The compounds of Formula I were shown to be potent $A_3$ adenosine receptor agonists in these assays.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:
1. A compound of the formula:

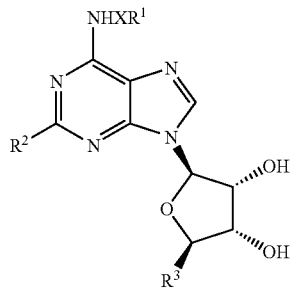

Formula I wherein:
R$^1$ is lower alkyl of 1–6 carbon atoms, cycloalkyl of 3–6 carbon atoms, or phenyl optionally substituted by halo;
X is a covalent bond or alkylene of 1–3 carbon atoms;
R$^2$ is R$^4$-Z-Y—C≡C— in which Y is alkylene of 1–3 carbon atoms, Z is oxygen, sulfur or —NH—, and R$^4$ is phenyl optionally substituted by halo or lower alkoxy; or
R$^2$ is pyrazolyl optionally substituted by phenyl or benzyl, which are optionally substituted by halo, lower alkyl, or lower alkoxy, or;
R$^2$ is pyrazolyl substituted by (lower alkyl)-O—C(O)—, —C(O)NH$_2$, —C(O)NH-(lower alkyl), cycloalkyl of 3–6 carbon atoms, pyrimidinyl, pyridinyl, benzoxazolyl, quinazolyl, isoquinazolyl, or pryrazolyl, said pyrimidinyl, pyridinyl, benzoxazolyl, quinazolyl, isoquinazolyl, or pryrazolyl all of which are optionally substituted by 1, 2 or 3 lower alkyl groups; and
R$^3$ is hydroxymethyl or —C(O)—NR$^5$R$^6$;
in which R$^5$ and R$^6$ are independently hydrogen or lower alkyl.
2. The compound of claim 1, wherein R$^2$ is pyrazol-1-yl substituted by phenyl, which is optionally substituted by halo, lower alkyl, or lower alkoxy.
3. The compound of claim 2, wherein R$^1$ is lower alkyl of 1–6 carbon atoms or phenyl optionally substituted by halo, and R$^3$ is hydroxymethyl.
4. The compound of claim 3, wherein R$^1$ is lower alkyl of 1–6 carbon atoms and X is a covalent bond.
5. The compound of claim 4, wherein R$^1$ is methyl and R$^2$ is 4-(4-methoxyphenyl)pyrazol-1-yl, namely (4S,2R,3R,5R)-5-(hydroxymethyl)-2-{2-[4-(4-methoxyphenyl)pyrazolyl]-6-(methylamino)purin-9-yl}oxolane-3,4-diol.
6. The compound of claim 4, wherein R$^1$ is n-propyl and R$^2$ is 4-(4-methoxyphenyl)pyrazol-1-yl, namely (4S,2R,3R,5R)-5-(hydroxymethyl)-2-{2-[4-(4-methoxyphenyl)pyrazolyl]-6-(n-propylamino)purin-9-yl}oxolane-3,4-diol.
7. The compound of claim 4, wherein R$^1$ is methyl and R$^2$ is 4-(4-chlorobenzylaminocarbonyl)pyrazol-1-yl, namely (1-{9-[(4S,2R,3R,5R)-3,4-dihydroxy-5-(hydroxymethyl)oxolan-2-yl]-6-(methylamino)purin-2-yl}pyrazol-4-yl)-N-(4-chlorophenyl)carboxamide.
8. The compound of claim 4, wherein R$^1$ is methyl and R$^2$ is 4-(4-chlorobenzylaminocarbonyl)pyrazol-1-yl, namely (1-{9-[(4S,2R,3R,5R)-3,4-dihydroxy-5-(hydroxymethyl)oxolan-2-yl]-6-(methylamino)purin-2-yl}pyrazol-4-yl)-N-(4-chlorophenyl)carboxamide.
9. The compound of claim 1, wherein R$^1$ is lower of 1–6 carbon atoms, R$^2$ is pyrazo-1-yl substituted by (lower alkyl)-O—C(O)—, —C(O)NH$_2$, —C(O)NH-(lower alkyl), cycloalkyl of 3–6 carbon atoms, pyrimidinyl, pyridinyl, benzoxazolyl, quinazolyl, isoquinazolyl, or pyrazolyl, said pyrimidinyl, pyridinyl, benzoxazolyl, isoquinazolyl, or pyrazolyl all of which are optionally substituted by 1, 2 or 3 lower alkyl groups, $R^3$ hydroxymethyl, and X is a covalent bond.

10. The compound of claim 9, wherein $R^1$ is n-propyl and $R^2$ is 4-(pyrid-2-yl)pyrazol-1-yl, namely (4S,2R,3R,5R)-5-(hydroxymethyl)-2-[4-(pyridin-2-yl)pyrazolyl]-6-(n-propylamino)purin-9-yl}oxolane-3,4-diol.

11. The compound of claim 3, wherein $R^1$ is phenyl optionally substituted by halo and X is methylene.

12. The compound of claim 11, wherein $R^1$ is 3-iodophenyl and $R^2$ is 4-(4-methoxyphenyl)pyrazol-1-yl, namely (4S, 2R,3R,5R)-5-(hydroxymethyl)-2-{2-[4-(4-methoxyphenyl)pyrazolyl]-6-(3-iodobenzylamino)purin-9-yl}oxolane-3,4-diol.

13. The compound of claim 1, wherein $R^2$ is pyrazol-4-yl optionally substituted by benzyl.

14. The compound of claim 13, wherein $R^1$ is lower alkyl of 1–6 carbon atoms and $R^3$ is hydroxymethyl.

15. The compound of claim 14, wherein $R^1$ is methyl, $R^2$ is 1-benzylpyrazol-4-yl, $R^3$ is hydroxymethyl, and X is a covalent bond, namely (4S,2R,3R,5R)-5-(hydroxymethyl)-2-{2-[1-benzylpyrazolyl]-6-(methylamino)purin-9-yl}oxolane-3,4-diol.

16. The compound of claim 14, wherein $R^1$ is n-propyll, $R^2$ is 1-benzylpyrazol-4-yl, $R^3$ is hydroxymethyl, and X is a covalent bond, namely (4S,2R,3R,5R)-5-(hydroxymethyl)-2-{2-[1-benzylpyrazolyl]-6-(n-propylamino)purin-9-yl}oxolane-3,4-diol.

17. The compound of claim 1, wherein $R^2$ is $R^4$-Z-Y—C≡C—.

18. The compound of claim 17, wherein $R^4$ is phenyl optionally substituted by halo or lower alkoxy, $R^3$ is hydroxymethyl, and Y is alkylene of 1–3 carbon atoms.

19. The compound of claim 18, wherein $R^4$ is phenyl optionally substituted by methoxy or chloro, and Y is methylene.

20. The compound of claim 19, wherein $R^1$ is alkyl of 1–6 carbon atoms, X is a covalent bond.

21. The compound of claim 20, wherein $R^1$ is methyl, $R^4$ is phenyl and Z is oxygen, namely 2-hydroxymethyl-5-[6-methylamino-2-(3-phenoxypropyn-1-yl)purin-9-yl]-tetrahydrofuran-3,4-diol.

22. A pharmaceutical composition comprising at least one pharmaceutically acceptable excipient and a terapheutically effective amount of a compound of claim 1.

* * * * *